United States Patent
Florent et al.

(10) Patent No.: US 10,603,004 B2
(45) Date of Patent: Mar. 31, 2020

(54) REVASCULARISATION LOCALISATION AND PRE AND POST QUANTITATIVE CORONARY ANGIOGRAPHY

(71) Applicant: KONINKLIJKE PHILIPS N.V., Eindhoven (NL)

(72) Inventors: Raoul Florent, Ville D'Avray (FR); Vincent Maurice André Auvray, Meudon (FR); Pierre Henri Lelong, Saint-Mande (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 136 days.

(21) Appl. No.: 15/747,045

(22) PCT Filed: Jul. 26, 2016

(86) PCT No.: PCT/EP2016/067755
§ 371 (c)(1),
(2) Date: Jan. 23, 2018

(87) PCT Pub. No.: WO2017/017086
PCT Pub. Date: Feb. 2, 2017

(65) Prior Publication Data
US 2018/0360407 A1 Dec. 20, 2018

(30) Foreign Application Priority Data
Jul. 27, 2015 (EP) ..................... 15306217

(51) Int. Cl.
*A61B 6/00* (2006.01)
*G06T 7/00* (2017.01)
(Continued)

(52) U.S. Cl.
CPC .......... *A61B 6/5217* (2013.01); *A61B 6/4441* (2013.01); *A61B 6/469* (2013.01);
(Continued)

(58) Field of Classification Search
CPC ..... A61B 6/5217; A61B 6/5235; A61B 6/503; A61B 6/487; A61B 6/469; A61B 6/4441;
(Continued)

(56) References Cited

U.S. PATENT DOCUMENTS

2008/0159610 A1  7/2008  Haas
2008/0242977 A1* 10/2008  Sirohey .............. A61B 5/02007
                                                    600/425
(Continued)

FOREIGN PATENT DOCUMENTS

JP   2013165874 A   8/2013
WO   2014111930 A1  7/2014

OTHER PUBLICATIONS

Woo, Jonghye, et al. "Nonlinear registration of serial coronary CT angiography (CCTA) for assessment of changes in atherosclerotic plaque." Medical physics 37.2 (2010): 885-896. (Year: 2010).*

(Continued)

*Primary Examiner* — Amandeep Saini

(57) ABSTRACT

The present invention relates to localization of a vascular treatment and quantification of a part of a vascular structure. It is described to provide (12) at least one first image comprising a representation of a region of interest of a vascular structure. At least one second image comprising a representation of the region of interest of the vascular structure is provided (14). Between an acquisition of the at least one first image and an acquisition of the at least one second image, a vascular treatment might have been applied to the region of interest of the vascular structure, wherein the representation of the region of interest of the vascular structure relates to spatial extension information of the vascular structure at least in one image plane. At least one reference image from an image set formed from the at least one first image and the at least one second image is selected (16). At least one sample image from the image set formed (Continued)

from the at least one first image and the at least one second image is selected (18), wherein the at least one sample image is different to the at least one reference image. At least one image from the at least one sample image is registered (20) with the at least one reference image to provide at least one registered image. It is determined (22) if there exists at least one region of spatial discrepancy between the representation of the region of interest in the at least one reference image and the representation of the region of interest in the at least one registered image. Data is output (24) representative of the at least one region of spatial discrepancy.

15 Claims, 7 Drawing Sheets

(51) Int. Cl.
    *G06T 7/62*     (2017.01)
    *A61B 6/03*     (2006.01)

(52) U.S. Cl.
    CPC .............. *A61B 6/487* (2013.01); *A61B 6/503* (2013.01); *A61B 6/504* (2013.01); *A61B 6/5235* (2013.01); *G06T 7/0016* (2013.01); *G06T 7/62* (2017.01); *A61B 6/032* (2013.01); *G06T 2207/10116* (2013.01); *G06T 2207/30101* (2013.01)

(58) Field of Classification Search
    CPC ........... A61B 6/504; A61B 6/032; G06T 7/62; G06T 7/0016; G06T 2207/10116; G06T 2207/30101
    USPC ........................................................ 382/128
    See application file for complete search history.

(56)             References Cited

U.S. PATENT DOCUMENTS

2008/0270423 A1    10/2008  Kargar
2014/0161331 A1    6/2014  Cohen
2014/0204124 A1    7/2014  Auvray

OTHER PUBLICATIONS

Woo, Jonghye et al "Nonlinear Registration of Serial Coronary CT Angiography (CCTA) for Assessment of Changes in Atherosclerotic Plaque", Medical Physics, vol. 37, No. 2, Jan. 2010, pp. 885-896.
Sanborn, Timotha A. et al "ACC/AHA/SCAI 2014 Health Policy Statement on Structured Reporting for the Cardiac Catheterization Laboratory". Journal of the American College of Cardiology, vol. 63, Issue 23, Jun. 2014.

* cited by examiner

REVASCULARISATION LOCALISATION AND PRE AND POST QUANTITATIVE CORONARY ANGIOGRAPHY

CROSS-REFERENCE TO PRIOR APPLICATIONS

This application is the U.S. National Phase application under 35 U.S.C. § 371 of International Application No. PCT/EP2016/067755, filed on Jul. 26, 2016, which claims the benefit of European Patent Application No. 15306217.9, filed on Jul. 27, 2015. These applications are hereby incorporated by reference herein.

FIELD OF THE INVENTION

The present invention relates to an apparatus for localization of a vascular treatment and quantification of a part of a vascular structure, to a medical system for localization of a vascular treatment and quantification of a part of a vascular structure, and to a method for localization of a vascular treatment and quantification of a part of a vascular structure, as well as to a computer program element and a computer readable medium.

BACKGROUND OF THE INVENTION

In vascular treatments, for example in Percutaneous Transluminal Coronary Angioplasty (PTCA) to treat cardiac stenosis, information relating to the vascular treatments is required to be provided. In particular, the clinician has to describe which stenosis was treated, for instance by localizing them onto acquired angiogram imagery. Furthermore, Quantitative Coronary Angiography (QCA) values of each stenosis before and after stenting are often required to be provided. The QCA value is the relative reduction of the artery diameter at the stenosis position. These values can be used to support the need for intervention, and to document the success or failure of the intervention. The clinician frequently has to select a sequence of angiograms obtained pre-intervention, i.e. before the actual intervention or treatment, and to select a frame from that sequence, to locate the stenosis, and to click several times on the frame with the mouse cursor in order to determine a QCA value. This also has to be conducted for a sequence of angiograms obtained post-intervention, i.e. after the intervention or treatment. Therefore, obtaining QCA values takes time, can be tedious, and as such is sometimes omitted or only roughly estimated visually. WO 2014/111930A1 discloses a method for vascular modelling. The method, in some embodiments, comprises receiving a plurality of 2-D angiographic images of a portion of a vasculature of a subject, and processing the images to automatically detect 2-D features, for example, paths along vascular extents.

US 2008/242977A1 describes systems, methods and apparatus through which in some embodiments detection of a change in characteristics of plaque in a longitudinal exam is automated for the purpose of assessing change in disease due to therapy, patient behavior modifications or follow-up. In some embodiments, diagnosis and treatment of arterial lesions includes obtaining a plurality of sets of computed-tomography images of at least one arterial plaque lesion, wherein each set of computed-tomography images are acquired at a different time, then storing the computed-tomography images in a database and analyzing arterial plaque variations in the sets of computed-tomography images for changes in at least one parameter.

SUMMARY OF THE INVENTION

It would be advantageous to have an improved technique for providing localization of a vascular treatment and quantitative coronary angiography values. The object of the present invention is solved with the subject matter of the independent claims, wherein further embodiments are incorporated in the dependent claims. It should be noted that the following described aspects of the invention apply also for the apparatus for localization of a vascular treatment and quantification of a part of a vascular structure, the medical system for localization of a vascular treatment and quantification of a part of a vascular structure, the method for localization of a vascular treatment and quantification of a part of a vascular structure, and for the computer program element and the computer readable medium.

According to a first aspect, there is provided an apparatus for vascular treatment localization and quantification, the apparatus comprising:
  an input unit;
  a processing unit; and
  an output unit.

The input unit is configured to provide at least one first image comprising a representation of a region of interest of a vascular structure, and to provide at least one second image comprising a representation of the region of interest of the vascular structure. Between an acquisition of the at least one first image and an acquisition of the at least one second image a vascular treatment might have been applied to the region of interest of the vascular structure. Further, the representation of the region of interest of the vascular structure relates to spatial extension information of the vascular structure at least in one image plane.

The processing unit is configured to select at least one reference image from an image set formed from the at least one first image and the at least one second image. The processing unit is also configured to select at least one sample image from the image set formed from the at least one first image and the at least one second image, wherein the at least one sample image is different to the at least one reference image. The processing unit is further configured to register at least one image from the at least one sample image with the at least one reference image to provide at least one registered image. Still further, the processing unit is configured to determine if there exists at least one region of spatial discrepancy between the representation of the region of interest in the at least one reference image and the representation of the region of interest in the at least one registered image.

The output unit is configured to output data representative of the at least one region of spatial discrepancy.

As a result, the location of the intervention can be automatically determined. Also, pre-intervention and post-intervention QCA values can be determined. This enables for it to be determined whether the intervention was carried out as expected, whether the intervention was successful, whether the intervention was deployed as expected, whether the post-intervention vascular structure is as expected, and hence to provide the clinician with the information required to support the need for the intervention and to document its success. Furthermore, this information can be automatically linked to the location of the treatment. Furthermore, angiogram images can be analysed to determine if a treatment has been applied between the acquisition of the first image and the acquisition of the second image. For example, if no spatial discrepancy exists it can be determined that no vascular treatment has occurred.

In an example, between an acquisition of the at least one first image and the acquisition of the at least one second image a vascular treatment has been applied to the region of interest of the vascular structure.

This means that when an angiogram is acquired, the search for spatial discrepancies can be conducted with respect to previously acquired angiogram imagery (that may have been acquired at the same angulation). If spatial discrepancies are determined to exist, the corresponding QCA values can be computed. If however, no spatial discrepancies are determined to exist then it is probable that no stenting has been performed.

The term "vascular treatment" relates to a procedure that has an effect on the vascular structure in terms of opening width available for blood-flow through the vascular segment(s). For example, vascular treatment relates to Percutaneous Transluminal Coronary Angioplasty (PTCA), or Percutaneous Coronary Intervention (PCI). For example, the use of interventional devices such as balloons for dilation and stent delivery and detachable coils for aneurysm clotting may be provided.

The term "reference image" relates to an image that is being used as a reference or baseline, useable in determining if another image has a region of spatial discrepancy. The reference image, or reference images, can be selected from those images acquired before the potential vascular treatment was applied or selected from those images acquired after the potential vascular treatment was applied. The reference image(s) can be selected as an image(s) that comprises image data representative of at least a part of a vascular structure in a visible and distinct manner. The term "visible and distinct" with respect to the at least a part of the vascular structure relates to at least part of the vascular structure being presented such that the vascular structure can be located and/or identified and/or delineated, either manually or automatically. The imagery, i.e. the images, can be visible and distinct due to contrast agent having been injected into the vascular structure at the time of image acquisition, for example during X-ray angiography.

The term "sample image" relates to an image selected from the images acquired before and after the potential vascular treatment was applied. The sample image is however an image, or images, different to the reference image. The sample images can be selected as those images wherein the at least one first image and/or the at least one second image comprise image data representative of at least a part of a vascular structure in a visible and distinct manner. The imagery can be acquired during X-ray angiography.

The term "registered image" relates to a sample image, or sample images, that has (have) been registered in relation to the reference image to form or provide the registered image. For example, sample image(s) can be registered with respect to cardiac cycle, patient breathing, patient motion, or image zooming, or any combination thereof. In an example, this leads to a spatially corresponding vessel tree between the registered image and the reference image. In other words, the vascular structure in the region of interest of the reference image is optimally similar to that of the registered image, or in other words the vessels in both images are as similar as possible, for example the centrelines of the vessels in both images are as similar as possible. The reference image and registered image are then useable in determining if there is a region of spatial discrepancy between these images.

The term "spatial discrepancy" relates to a region of the vascular structure between the reference and registered image that is not optimally similar. For example, following registration the vascular structure between the reference and registered image could be similar everywhere, except for one region. In that region, for example, the artery could be narrow in the reference image but widened out in the registered image. This indicates that there is a stenosis at that location, which has yet to be treated in the reference image but has been treated in the sample image that led to the registered image. The treatment could, for example, have been provided through the use of a balloon to open out the artery and deploy a stent.

The term "automatic" may relate to the system being able to perform the action or step without the immediate need of a user input. In a method, the step is performed providing the result or output based on the input, but without further user interaction. In an example, the apparatus is referred to as an apparatus for automatic quantification of a part of a vascular structure.

In an example, the processing unit is configured to determine if there is a discrepancy in a size of a feature at a location in the representation of the region of interest in the at least one reference image with respect to the feature at the same location in the representation of the region of interest in the at least one registered image.

The term "feature" relates to a region or artifact in the imagery. For example, the feature can relate to the vascular structure. In an example, the feature relates to a stenosis in an artery in a reference image, and the registered image relates to an image where the stenosis has been treated. Therefore, the discrepancy in size of the feature at a location can relate to the vascular structure being constricted in the reference image and the vascular structure at that location being opened out or widened in the registered image. In another example, the stenosis can be visible in the registered image and the treated stenosis can be visible in the reference image.

In an example, the discrepancy in the size of the feature is a discrepancy in the diameter of the feature; and the processing unit is configured to determine the relative change in the diameter of the feature in the at least one reference image with respect to the at least one registered image.

This enables the QCA information pre and post the vascular treatment to be determined. Therefore, it can be determined if the treatment was imperfect, and the stenosis only partially reopened. Also, information is automatically provided enabling the clinician to show that the treatment was necessary.

In an example, the discrepancy in size or diameter is only determined at a spatial position corresponding to a position of the vascular structure.

The term "position of the vascular structure" relates to a position at or on the vascular structure. Locations with discrepancies that are located remote from the vascular structure are not further considered in an example.

In an example, the processing unit is configured to select at least two sample images; and to provide at least two registered images. The processing unit is also configured to verify that a region of spatial discrepancy exists if a discrepancy in the size or diameter of the feature is present in a first of the at least two registered images, and that a discrepancy in the size or diameter of the feature is present in at least a second of the at least two registered images. In other words, it is determined if a discrepancy at a particular location exists in more than one angiogram.

For example, the processing unit can select 10 sample images and provide 10 registered images, and a region of spatial discrepancy is verified to exist if a discrepancy in the size or diameter of the feature is present in two of those registered images.

In an example, a region of spatial discrepancy is verified to exist if a discrepancy in the size or diameter of the feature is present in more than two of those registered images. In an example, the processing unit can select "n" sample images and provide "n" registered images, and a region of spatial discrepancy is verified to exist if a discrepancy in the size or diameter of the feature is present in a number "p" of those images, where p=n/2. In an example, a region of spatial discrepancy is verified to exist if a discrepancy in the size or diameter of the feature is present in a number "p" of those images, where p=2n/3. In an example, a region of spatial discrepancy is verified to exist if a discrepancy in the size or diameter of the feature is present in a number "p" of those images, where n≥p≥1. In an example, a region of spatial discrepancy is verified to exist if a discrepancy in the size or diameter of the feature is present in two consecutive registered images. In an example, a region of spatial discrepancy is verified to exist if a discrepancy in the size or diameter of the feature is present in three consecutive registered images. In an example, a region of spatial discrepancy is verified to exist if a discrepancy in the size or diameter of the feature is present in four consecutive registered images. In an example, a region of spatial discrepancy is verified to exist if a discrepancy in the size or diameter of the feature is present in more than four consecutive registered images.

Therefore, discrepancies in the size or diameter of vascular features in more than one angiogram are looked for in order to verify (or validate) that there is a region of spatial discrepancy, or possibly invalidate that there is a region of spatial discrepancy or in other words determine that no region of spatial discrepancy exists. Or, put another way those diameter-high-discrepancy areas can be tracked along the temporal axis of the angiograms in order to re-enforce the identification robustness.

In an example, it is provided at least one of the group of: the processing unit is configured to select the at least one reference image from the at least one first image; and the processing unit is configured to select the at least one sample image from the at least one second image.

By choosing the reference frame, from images acquired before treatment, a stenosis is more visible at this stage, providing for better visual interpretation of any resultant imagery.

In an example, the processing unit is configured to provide the at least one registered image through the application of a transform to the at least one sample image.

In other words, a first image (such as an angiogram), other than a reference image (such as an angiogram), undergoes a spatial transform before determining if there is a spatial discrepancy between that first image angiogram and the reference angiogram. This can account for cardiac cycle, breathing, patient-motion, possible zooming and can also account for angiograms taken for example with different angulation. In an example, the spatial transform comprises a 3D spatial transform.

In an example, the at least one sample image comprises a plurality of sample images, and the transform is a spatial-temporal pairing transform. In this example, the processing unit is configured to provide the at least one registered image, comprises pairing a sample image of the at least one sample image with the at least one reference image.

In an example, the at least one reference image comprises a plurality of reference images and the transform is a spatial-temporal pairing transform. In this example, the processing unit is configured to provide the at least one registered image and comprises pairing a sample image of the at least one sample image with a reference image of the at least one reference image.

In other words, a reference image is paired with a sample image in providing the registered image. In doing this, an image is selected where features in the images closely match. Therefore, the spatial-temporal pairing transform automatically accounts for patient movement such as breathing, and automatically accounts for movement such as the cardiac cycle. In other words, both spatial and temporal transformations occur, where images are paired temporally so that they correspond to the same heart phase, and then the registered spatially to account for breathing. Furthermore, this occurs without it being necessary to determine either the point or phase in the breathing cycle or the point or phase in the cardiac cycle.

According to a second aspect, there is provided a medical system for vascular treatment localization and quantification, the system comprising:
an image acquisition unit; and
an apparatus for vascular treatment localization and quantification according to any one of the preceding claims.

The image acquisition unit is configured to provide the at least one first image and the at least one second image comprising the representation of the region of interest of the vascular structure before and after a vascular treatment.

By providing a medical system for vascular treatment localization and quantification, the clinician is automatically provided with the required reporting information associated with the intervention. The clinician is provided with information regarding which stenosis was treated, and where that stenosis is located within the vascular structure over an angiogram image. They are provided with information regarding the severity of stenosis prior to the interventions, and whether the interventions have been successful. They do not need to manually determine QCA values relating to the intervention, which would require assessing angiography image frames both before and after that intervention, with a manual determination of where the intervention was performed within those images also having to be undertaken. They are also provided with information regarding whether an intervention has occurred between sets of acquired images.

In an example, the medical system is referred to as a medical system for automatic quantification of a part of a vascular structure.

According to a third aspect, there is provided a method for vascular treatment localization and quantification, comprising:
a) providing at least one first image comprising a representation of a region of interest of a vascular structure;
b) providing at least one second image comprising a representation of the region of interest of the vascular structure;
wherein, between an acquisition of the at least one first image and an acquisition of the at least one second image, a vascular treatment might have been applied to the region of interest of the vascular structure; and wherein the representation of the region of interest of the vascular structure relates to spatial extension information of the vascular structure at least in one image plane;

c) selecting at least one reference image from an image set formed from the at least one first image and the at least one second image;

d) selecting at least one sample image from the image set formed from the at least one first image and the at least one second image, wherein the at least one sample image is different to the at least one reference image;

e) registering at least one image from the at least one sample image with the at least one reference image to provide at least one registered image;

f) determining if there exists at least one region of spatial discrepancy between the representation of the region of interest in the at least one reference image and the representation of the region of interest in the at least one registered image; and g) outputting of data representative of the at least one region of spatial discrepancy.

The term "angiogram" relates to a visualization of the blood vessels of the heart region, and, alternatively or in addition, a vascular structure outside of the heart of the patient.

In an example, the method is referred to as a method for automatic quantification of a part of a vascular structure, In an example, step f) comprises a sub-step f1) of determining if there is a discrepancy in a size of a feature at a location in the representation of the region of interest in the at least one reference image with respect to the feature at the same location in the representation of the region of interest in the at least one registered image.

In an example, step e) comprises a sub-step e1) of applying a transform to the at least one sample image.

According to a fourth aspect, there is provided a computer program element controlling a device, i.e. an apparatus or a system, as previously described which, when the computer program element is executed by a processing unit, is adapted to perform the method steps as previously described.

According to fifth aspect, there is provided a computer readable medium having stored a computer element as previously described.

Advantageously, the benefits provided by any of the above aspects equally apply to all of the other aspects and vice versa.

The above aspects and examples will become apparent from and be elucidated with reference to the embodiments described hereinafter.

BRIEF DESCRIPTION OF THE DRAWINGS

Exemplary embodiments will be described in the following with reference to the following drawings.

DETAILED DESCRIPTION OF EMBODIMENTS

Figure 1:
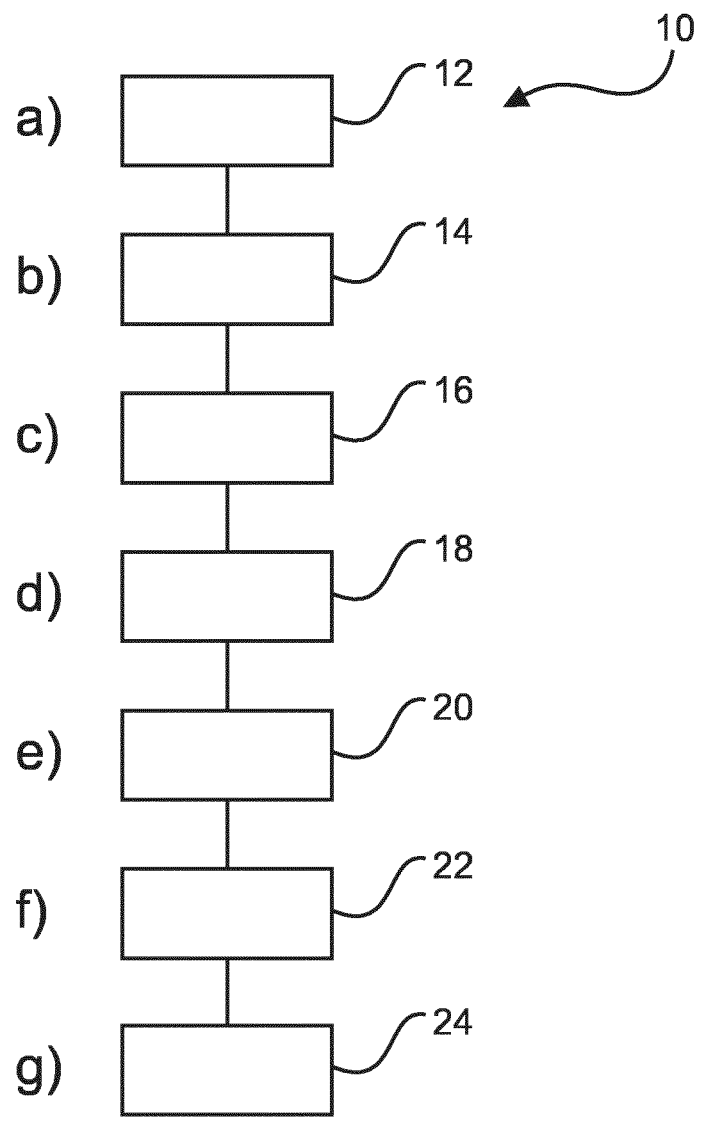
FIG. 1 shows an example of a method for vascular treatment localization and quantification of a part of a vascular structure.

FIG. 1 shows a method 10 for automatic vascular treatment localization and quantification of a part of a vascular structure in its basic step. The method 10 comprises the following:

In a first providing step 12, also referred to as step a), at least one first image comprising a representation of a region of interest of a vascular structure is provided.

In a second providing step 14, also referred to as step b), at least one second image comprising a representation of the region of interest of the vascular structure is provided.

Between an acquisition of the at least one first image and an acquisition of the at least one second image, a vascular treatment might have been applied to the region of interest of the vascular structure. The representation of the region of interest of the vascular structure relates to spatial extension information of the vascular structure at least in one image plane.

In a first selecting step 16, also referred to as step c), at least one reference image from an image set formed from the at least one first image and the at least one second image is selected.

In a second selecting step 18, also referred to as step d), at least one sample image from the image set formed from the at least one first image and the at least one second image is selected. The at least one sample image is different to the at least one reference image.

In a registering step 20, also referred to as step e), at least one image from the at least one sample image is registered with the at least one reference image to provide at least one registered image.

In a determining step 22, also referred to as step f), it is determined if there exists at least one region of spatial discrepancy between the representation of the region of interest in the at least one reference image and the representation of the region of interest in the at least one registered image.

In an outputting step 24, also referred to as step g), data representative of the at least one region of spatial discrepancy is output, e.g. provided to a user.

In an example, between the acquisition of the at least one first image and the acquisition of the at least one second image, a vascular treatment has been applied to the region of interest of the vascular structure.

In an example, the at least one first image is an angiogram. In an example, the at least one second image is an angiogram.

In an example, the vascular treatment results in, or at least aims at, there being at least one region of spatial discrepancy. In other words, the vascular treatment leads to a difference in the vascular dimensions in relation to the flow-through characteristics.

In an example, the vascular treatment was for the treatment of a stenosis. For example, the region of spatial discrepancy is at the position of the stenosis and the spatial discrepancy results from the vascular treatment having been applied at the location of the stenosis after the at least one first image was acquired and before the at least one second image was acquired.

In an example, a stenosis is well-visible within the at least one first image. The term "well-visible" relates to the stenosis being present within the at least one first image such that it can be identified, either manually or automatically. In other words, the vascular structure in the at least one first image is shown in a visible and distinct manner. In an example, the location of the stenosis, post treatment, is well-visible within the at least one second image. In other words, the vascular structure in the at least one second image is shown in a visible and distinct manner.

In another example, the location of the stenosis, post treatment, is not identifiable itself, e.g. not visible, within the at least one second image, but can be identified by the discrepancy determination, or result of comparison.

In an example, a reference image is selected from the at least one first image and a sample image is selected from the at least one second image. The sample image is then registered toward the reference image, to yield a registered image—a transformed version of the sample image, aligned with the reference.

In an example, the at least one first image comprises a plurality of first images acquired before the vascular treatment was applied.

In an example, the at least one second image comprises a plurality of second images acquired after the vascular treatment was applied.

In an example, the plurality of first images were acquired over a range of system angulations, and step a) comprises grouping first images together into groups acquired with similar system angulations—a group can comprise one image. In an example, step a) further comprises providing the at least one first image as a group of first images acquired at one, or over a limited range of, system angulation.

In an example, the plurality of second images were acquired over a range of system angulations, and step b) comprises grouping second images together into groups acquired with similar system angulations—a group can comprise one image. In an example, step b) further comprises providing the at least one second image as a group of second images acquired at one, or over a limited range of, system angulation. In an example, step b) further comprises providing the at least one second image as a group of second images acquired at the same, or over the same limited range of, system angulation, as that for the group of first images.

When grouping images, for example angiograms, into groups having the same angulation, a certain tolerance can be fixed and small angulation deviations accepted—this is what is meant by "a limited range of system angulation".

In an example, the at least one first and/or the at least one second images (as selected sample images) are registered with respect to at least one of the following: cardiac-cycle, breathing, patient-motion and zooming.

In an example, the at least one first and/or the at least one second images are acquired as a plurality of images in the form of image sequences. For example, each sequence can comprise a number of separate images acquired over one or more complete heart cycles. Therefore, in an example, registration has a spatial element and can account for patient breathing, motion and image zooming, and registration has a temporal element and can account for the patient's cardiac cycle.

In an example, step c) and/or step d) comprises discarding first images that are non-injected or insufficiently injected images. In an example, this example further comprises retaining first images that correspond to a well-injected cardiac cycle. In an example, this example further comprises retaining first images that are consecutive images that correspond to a well-injected cardiac cycle.

In an example, step c) and/or step d) comprises discarding second images that are non-injected or insufficiently injected images. In an example, this example further comprises retaining second images that correspond to a well-injected cardiac cycle. In an example, this example further comprises retaining second images that are consecutive images that correspond to a well-injected cardiac cycle.

In an example, every significant spatial discrepancy is an indicator of a stenosis treatment.

In an example, the registered image is determined to be the sample image.

In an example, step c) further comprises selecting the at least one reference image on the basis of the image that constitutes the best injected imagery.

In an example, step d) further comprises selecting at least one sample image on the basis of the image or images that constitutes the best injected imagery.

In an example, step f) comprises determining reference image coordinates for the location of the at least one region of spatial discrepancy.

In an example, step f) comprises determining registered image coordinates for the location of the at least one region of spatial discrepancy.

In an example, step g) comprises outputting data representative of a localization of the at least one region of spatial discrepancy in the region of interest of the vascular structure; for example, by displaying the localization of the at least one region of spatial discrepancy on the at least one reference image or on an image other than the at least one reference image. In an example, the location of every significant spatial discrepancy is localized on an angiogram.

In an example, step g) comprises outputting Quantitative Coronary Angiography (QCA) information relating to the at least one region of spatial discrepancy. In an example, QCA information is provided for every significant spatial discrepancy. In an example, QCA information is provided for every significant spatial discrepancy both pre and post intervention.

Figure 2:
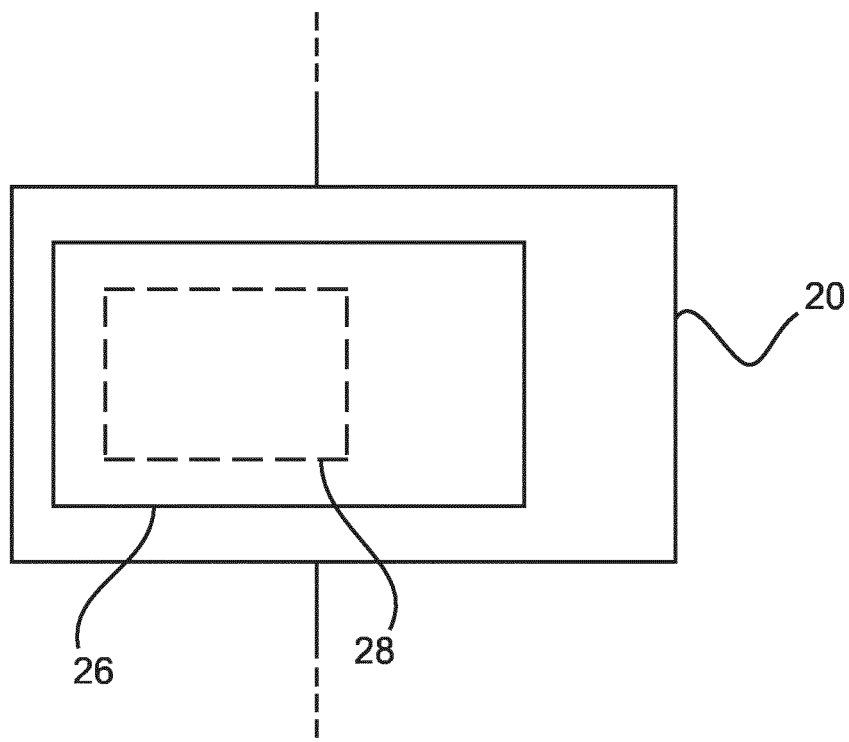
FIG. 2 shows an example of a method step involved in a method for vascular treatment localization and quantification of a part of a vascular structure.

FIG. 2 shows an example of a method step 20, step e), involved in a method for automatic vascular treatment localization and quantification of a part of a vascular structure. According to an example, step e) of the method comprises a sub-step 26, also referred to as step e1), of applying a transform to the at least one sample image.

In an example, providing at least one registered image comprises at least some features (e.g. A, B, C) in the at least one sample image becoming aligned with or being projected onto at least some similar features (e.g. A', B', C') in the at least one reference image.

In an example, the at least one sample image was acquired at the same angulation as the at least one reference image. For example, both acquisitions are performed with the same C-arm angulation. This provides for ease of determining if there exists at least one region of spatial discrepancy—step f).

In an example, sub-step e1) comprises overlaying the at least one sample image onto the at the least one reference image, and spatially moving the at least one sample image in the x- and/or y-directions until features in the at least one sample image most closely match features in the at least one reference image. In an example, any one or combination of different types of motions can be used: translations, rotations, zooming, or more local deformations.

In an example, sub-step e1) comprises transforming a size of at least one vascular feature in the representation of the region of interest in the at least one sample image to a size of the at least one vascular feature in the representation of the region of interest in the at least one reference image. In an example, the transforming comprises a linear transforming. For example, the spatial transform comprises an affine transformation, relating to, in particular, translations, rotations, and zooming. In an example, the transforming comprises a non-linear transforming. In an example, the at least one sample image is linearly or non-linearly stretched in the y- and/or x-directions until features in the at least one sample image most closely match features in the at least one reference image. In an example, at the same time as warping or stretching the sample image in the x- and/or y-directions, the sample image is moved in the x- and/or y-directions until features in the at least one sample image most closely match features in the at least one reference image.

In an example, sub-step e1) comprises the at least one sample image becoming optimally similar to the at least one reference image, such that a majority of the vascular features in the region of interest in the at least one sample image have the size of the same vascular features in the region of interest in the at least one reference image.

According to an example, the at least one sample image comprises a plurality of sample images, and the transform is a spatial-temporal pairing transform. In this example, sub-step 26, step e1), comprises step 28a of providing a registered image by pairing a sample image of the at least one sample image with the at least one reference image.

According to an example, the at least one reference image comprises a plurality of reference images and the transform is a spatial-temporal pairing transform. In this example, sub-step 26, step e1), comprises step 28b of providing a registered image by pairing a sample image of the at least one sample image with a reference image of the at least one reference image. In FIG. 2, steps 28a and 28b are represented by box 28.

In an example, sub-step e1) comprises pairing each sample image of the at least one sample image with a corresponding reference image of the at least one reference image.

In an example, the registered image set is provided through each image in the sample image set being paired and aligned with an image in the reference image set, where the paired images are optimally similar. By "optimally similar" it is meant that the vessels in the paired images are as similar as possible. Therefore, the spatial-temporal pairing transform accounts for cardiac cycle, patient breathing, patient motion and system zooming.

Figure 3:
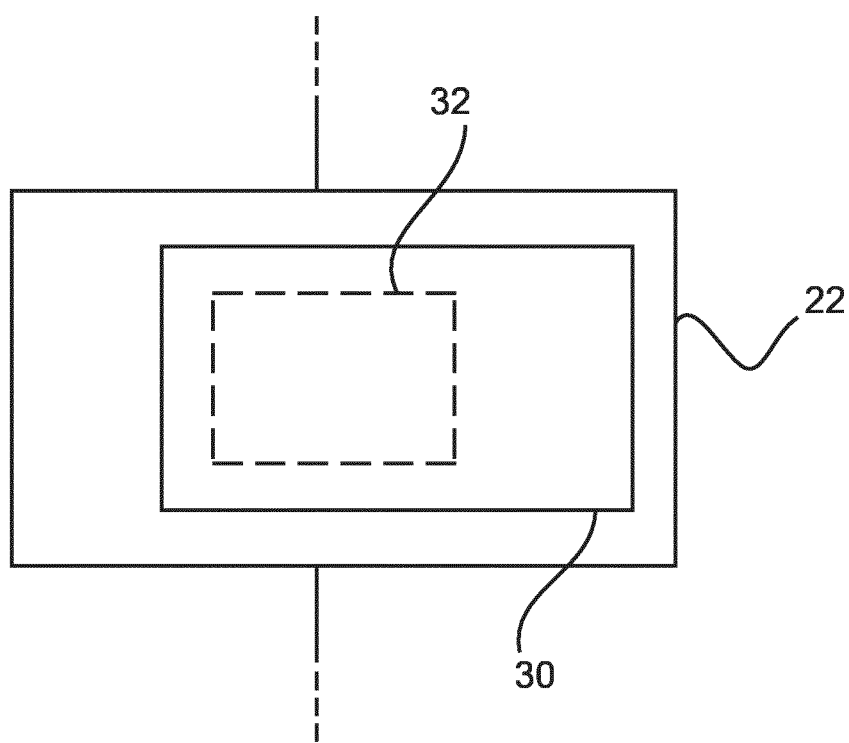
FIG. 3 shows an example of a method step involved in a method for vascular treatment localization and quantification of a part of a vascular structure.

FIG. 3 shows an example of a method step 22, step f), involved in a method for automatic vascular treatment localization and quantification of a part of a vascular structure.

According to an example, step 22, step f), comprises a sub-step 30, also referred to as step f1). In step 30 it is determined if there is a discrepancy in a size of a feature at a location in the representation of the region of interest in the at least one reference image with respect to the feature at the same location in the representation of the region of interest in the at least one registered image.

In an example, the determining comprises comparing the system angulation for the at least one registered image with the system angulation for the at least one reference image. This enables, for example, images acquired at the same or substantially the same system angulation to be used. In another example, this enables information regarding a difference in system angulation between the registered image and the reference to be taken into account.

According to an example, step 30, step f1), comprises step 32 of determining the relative change in the diameter of the feature in the at least one reference image with respect to the at least one registered image.

In an example, the discrepancy in size or diameter is only determined at a spatial position corresponding to a position of the vascular structure.

Figure 4:
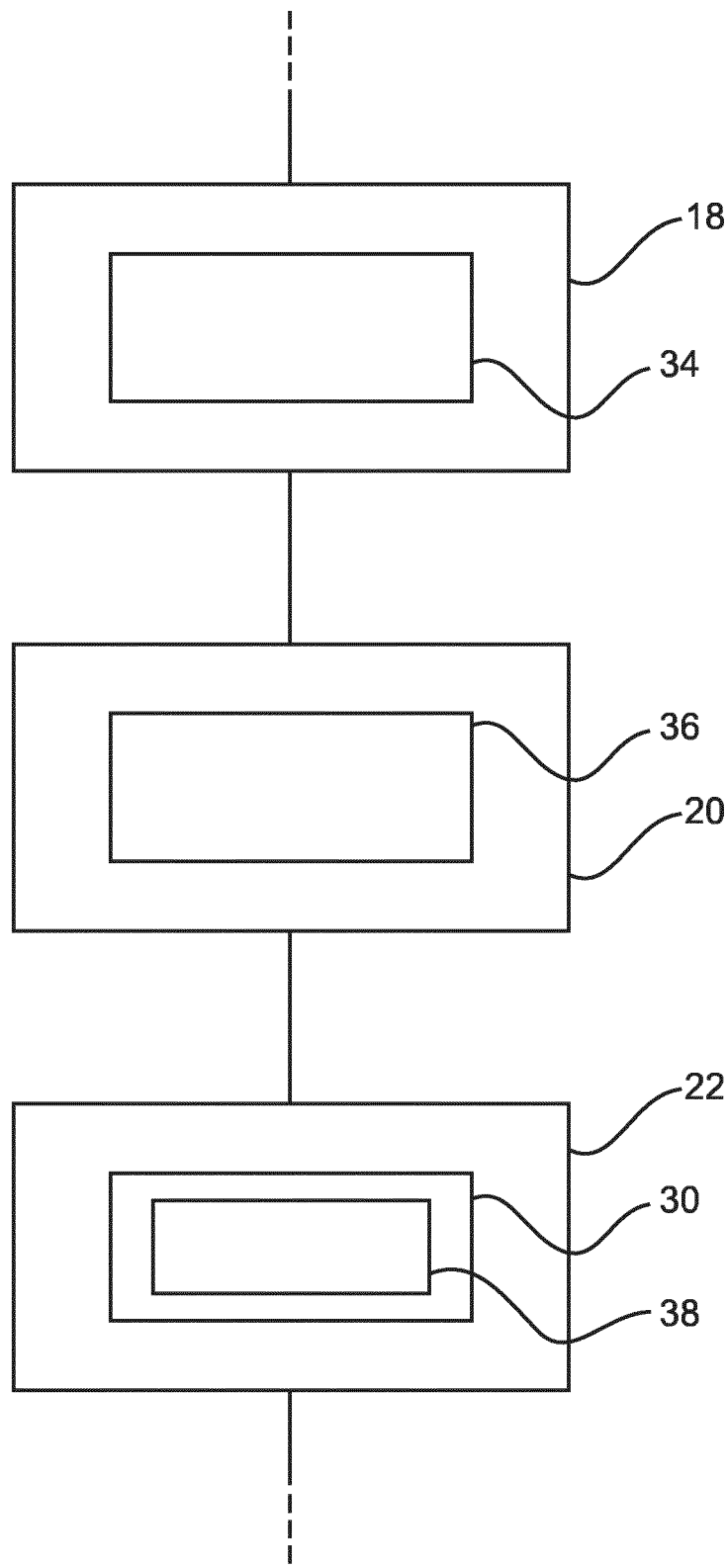
FIG. 4 shows an example of method steps involved in a method for vascular treatment localization and quantification of a part of a vascular structure.

FIG. 4 shows an example of method steps 18, 20, and 22 (d, e, and f respectively) involved in a method for automatic vascular treatment localization and quantification of a part of a vascular structure. According to an example, step d) comprises a selecting step 34 of selecting at least two sample images. In this example, step e) comprises a providing step 36, where at least two registered images are provided. Step f, which in this example comprises sub step f1) (step 30), then further comprises a verifying step 38 comprising verifying that a region of spatial discrepancy exists if a discrepancy in the size or diameter of the feature is present in a first of the at least two registered images, and if a discrepancy in the size or diameter of the feature is present in at least a second of the at least two registered images.

According to an example, step c) comprises selecting the at least one reference image from the at least one first image, and alternatively or additionally step d) comprises selecting the at least one sample image from the at least one second image.

Figure 5:
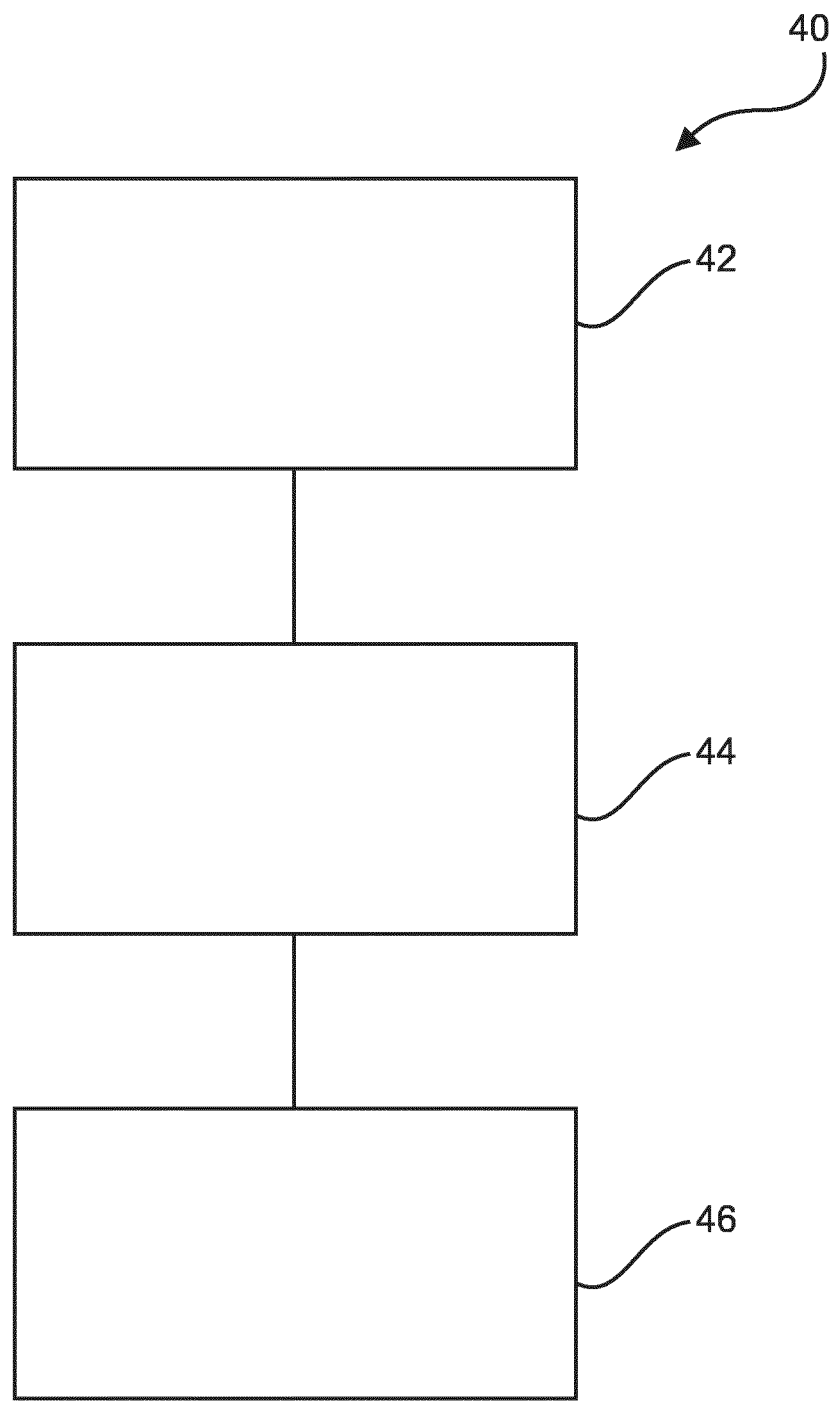
FIG. 5 shows a schematic set up an example of an apparatus for vascular treatment localization and quantification of a part of a vascular structure.

FIG. 5 shows an example of an apparatus 40 for automatic vascular treatment localization and quantification of a part of a vascular structure. The apparatus 40 comprises an input unit 42, a processing unit 44, and an output unit 46.

The input unit 42 is configured to provide the processing unit 44 with at least one first image comprising a representation of a region of interest of a vascular structure. The input unit 42 is also configured to provide the processing unit 44 with at least one second image comprising a representation of the region of interest of the vascular structure. Between an acquisition of the at least one first image and an acquisition of the at least one second image, a vascular treatment might have been applied to the region of interest of the vascular structure. It is to be noted that the representation of the region of interest of the vascular structure relates to spatial extension information of the vascular structure at least in one image plane.

The processing unit 44 is configured to select at least one reference image from an image set formed from the at least one first image and the at least one second image. The processing unit 44 is also configured to select at least one sample image from the image set formed from the at least one first image and the at least one second image. Here, the at least one sample image is different to the at least one reference image. The processing unit 44 is further configured to register at least one image from the at least one sample image with the at least one reference image to provide at least one registered image. Also, the processing unit 44 is configured to determine if there exists at least one region of spatial discrepancy between the representation of the region of interest in the at least one reference image and the representation of the region of interest in the at least one registered image.

The output unit 46 is configured to output data representative of the at least one region of spatial discrepancy.

In an example, the at least one first image comprises an angiogram. In an example, the at least one second image comprises an angiogram.

In an example, the at least one first image is based on X-ray radiation. For example, contrast agent is present during the acquisition of the at least one first image. For example, contrast agent has been injected into at least a part of the vascular structure in order to provide image data of the vascular structure in a visible and distinct manner.

In an example, the at least one second image is based on X-ray radiation. For example, contrast agent is present during the acquisition of the at least one second image. For example, contrast agent has been injected into at least a part of the vascular structure in order to provide image data of the vascular structure in a visible and distinct manner.

In an example, the at least one first image is of the same image type as the at least one second image.

In an example, the at least one first image comprises a sequence of first images.

In an example, the at least one second image comprises a sequence of second images.

In an example, the processing unit is configured to determine if there is a region of spatial discrepancy through the use of an image processor or image processing unit.

In an example, the processing unit is configured to select the at least one reference image from the at least one first image.

In an example, the at least one region of spatial discrepancy results from the vascular treatment having been applied.

In an example, the vascular treatment has been applied at a location of a stenosis.

In an example, a Quantitative Coronary Angiography (QCA) is performed using the at least one first image. The QCA is the ratio of a smaller diameter segment of a vessel compared to a reference diameter. The reference diameter is the diameter the vessel should have had at that location if it were healthy, and is taken to be the diameters of the vessel spatially either side of the stenosis.

In an example, a QCA is performed using the at least one second image.

In an example, the at least one first image and the at least one second image are acquired at the same angulation.

In an example, the vascular treatment is a revascularization. In an example, both pre and post revascularization images are present.

In an example, the output data relates to providing information relating to a stenosis, or other anomaly. For example, the outputting of data involves displaying or providing information on the localization of the at least one region of spatial discrepancy and/or providing quantitative information on the stenosis or anomaly, such as outputting QCA values.

According to an example, the processing unit is configured to determine if there is a discrepancy in a size of a feature at a location in the representation of the region of interest in the at least one reference image with respect to the feature at the same location in the representation of the region of interest in the at least one registered image.

In other words, it is changes in the size of features between the reference angiogram and an angiogram other than the reference that are used to determine if there is a region of spatial discrepancy.

In an example, each sample image of the at least one sample image is compared to its counterpart (the paired reference image of the at least one reference image). In other words, each registered image of the at least one registered image is compared to its paired reference image in order to determine if there is a discrepancy in size of a feature between those images.

In an example, the discrepancy in the size of the vascular feature is a discrepancy in the diameter of the vascular feature, and the processing unit is configured to determine the relative change in the diameter of the vascular feature in the at least one reference image with respect to the at least one registered image.

In an example, at every location in the at least one registered image, a size of a feature at that location is determined, and this size is compared to a size of the feature at the same location in the at least one reference image. In an example, a difference in size is determined at every location. In another example, a difference in size is measured only over a subpart of the image, for instance over a mask covering the structure of interest (for instance, a binary mask of the vessels of the image, or over a centerline of the vessels). In an example, a difference image is determined corresponding to the registered image, where at each position on the registered image the difference in size between the registered image at that location and the reference image at that location is presented.

According to an example, the discrepancy in the size of the feature is a discrepancy in the diameter of the feature. Then, the processing unit is configured to determine the relative change in the diameter of the feature in the at least one reference image with respect to the at least one registered image.

In other words, we are looking for a discrepancy in the diameter of a vascular feature and that the relative change in diameter of the vascular feature is determined between the reference angiogram and the angiogram other than the reference. In an example, the diameter of the feature in the reference and angiogram is compared against the diameter the vessel should have had at that location. For example, for a reference image that is selected as a first image, the diameter of the feature, such as a stenosis, is compared against the diameter of the artery either side of the stenosis. This is then conducted for the registered image, at the location of the treated stenosis. As discussed above, this then enables the QCA information pre and post the vascular treatment to be determined.

According to another example, the discrepancy in size or diameter is only determined at a spatial position corresponding to a position of the vascular structure. The term "position of the vascular structure" relates to a position at or on the vascular structure. Locations with discrepancy that are located remote from the vascular structure are not further considered. In other words, difference calculations are only required to be determined for a fraction of the image at the locations of the vascular structure—at salient locations. This leads to processing efficiencies, and furthermore any perturbations outside of the vascular structure are ignored, which otherwise could lead to spurious results.

According to an example, the processing unit is configured to select at least two sample images, and to provide at least two registered images. The processing unit is then further configured to verify that a region of spatial discrepancy exists if a discrepancy in the size or diameter of the feature is present in a first of the at least two registered images, and if a discrepancy in the size or diameter of the feature is present in at least a second of the at least two registered images. For example, the processing unit can select 10 sample images and provide 10 registered images, and a region of spatial discrepancy is verified to exist if a discrepancy in the size or diameter of the feature is present in two of those registered images.

In an example, the at least two sample images are selected from two consecutive first images that correspond to a well-injected cardiac cycle. In an example, the at least two sample images are selected from two consecutive second images that correspond to a well-injected cardiac cycle. In an example, the at least two sample images are selected from two non-consecutive first images that correspond to a well-injected cardiac cycle. In an example, the at least two sample images are selected from two non-consecutive second images that correspond to a well-injected cardiac cycle.

According to an example, the processing unit is configured to select the at least one reference image from the at least one first image. Alternatively, or additionally, the processing unit configured to select the at least one sample image from the at least one second image. By choosing the reference frame, from images acquired before treatment, a stenosis is more visible at this stage, providing for better visual interpretation of any resultant imagery.

According to an example, the processing unit is configured to provide the at least one registered image through the application of a transform to the at least one sample image.

In an example, the transform is a spatial or spatial-temporal transform.

In an example, application of the transform comprises a size of at least one vascular feature in the representation of the region of interest in the at least one sample image being transformed to a size of the at least one vascular feature in the representation of the region of interest in the at least one reference image In an example, application of the transform comprises the at least one sample image becoming optimally similar to the at least one reference image, such that a majority of the vascular features in the region of interest in the at least one sample image have the size of the same vascular features in the region of interest in the at least one reference image.

According to an example, the at least one sample image comprises a plurality of sample images, and the transform is a spatial-temporal pairing transform. The processing unit being configured to provide the at least one registered image then comprises pairing a sample image of the at least one sample image with the at least one reference image.

According to an example, the at least one reference image comprises a plurality of reference images and the transform is a spatial-temporal pairing transform. The processing unit being configured to provide the at least one registered image then comprises pairing a sample image of the at least one sample image with a reference image of the at least one reference image.

In an example, pairing the sample image with the reference image comprises determining the reference image of the plurality of reference images that most closely corresponds spatially to the sample image. For example, the vascular structure in the paired reference image is the vascular structure that most closely matches the vascular structure in the sample image.

In an example, the spatial- or spatio-temporal pairing transform comprises a spatial pairing transform and a temporal pairing transform. In an example, the spatial pairing transform is used to provide a rough, or tentative, spatial alignment between the at least one sample image and the at least one reference image as part of providing the at least one registered image. In an example, the plurality of sample images are comprised of image sequences, each sequence having individual image frames, where the individual image frames are acquired over one or more complete cardiac cycles. In an example, the spatial pairing transform is configured to pair an individual reference image with a sample sequence that is spatially similar to the reference image. The temporal-pairing transform is then configured to pair the reference image with the most similar sample image within the sequence. In an example, the plurality of reference images are comprised of image sequences, each sequence having individual image frames, where the individual image frames are acquired over one or more complete cardiac cycles. In an example, the spatial pairing transform is configured to pair a reference image sequence with a sample sequence that is spatially similar to the reference image sequence. The temporal-pairing transform is then configured to pair a reference image of the reference sequence with the most similar sample image within the sample sequence. In this manner, the spatial-pairing transform can account for patient breathing, patient motion and system zooming, and the temporal-pairing transform can account for the patient's cardiac cycle.

In an example, the processing unit is configured to provide the at least one registered image comprises pairing each sample image of the at least one sample image with a corresponding reference image of the at least one reference image.

In an example, the registered image set is provided through each image in the sample image set being paired and aligned with an image in the reference image set, where the paired images are optimally similar. By "optimally similar" it is meant that the vessels in the paired images are as similar as possible. Therefore, the spatial-temporal pairing transform accounts for cardiac cycle, patient breathing, patient motion and system zooming.

In an example, the output unit is configured to output data representative of a localization of the at least one region of spatial discrepancy in the region of interest of the vascular structure. In an example, the output unit is configured to display the localization of the at least one region of spatial discrepancy on the at least one reference image.

In an example, the output unit is configured to display stenting locations.

In an example, the output unit is configured to output QCA information derived from the at least one first image. In an example, the output unit is configured to output QCA information derived from the at least one second image.

In an example, the output unit is configured to output pre and post intervention (vascular treatment) QCA information associated with the stenting locations.

Figure 6:
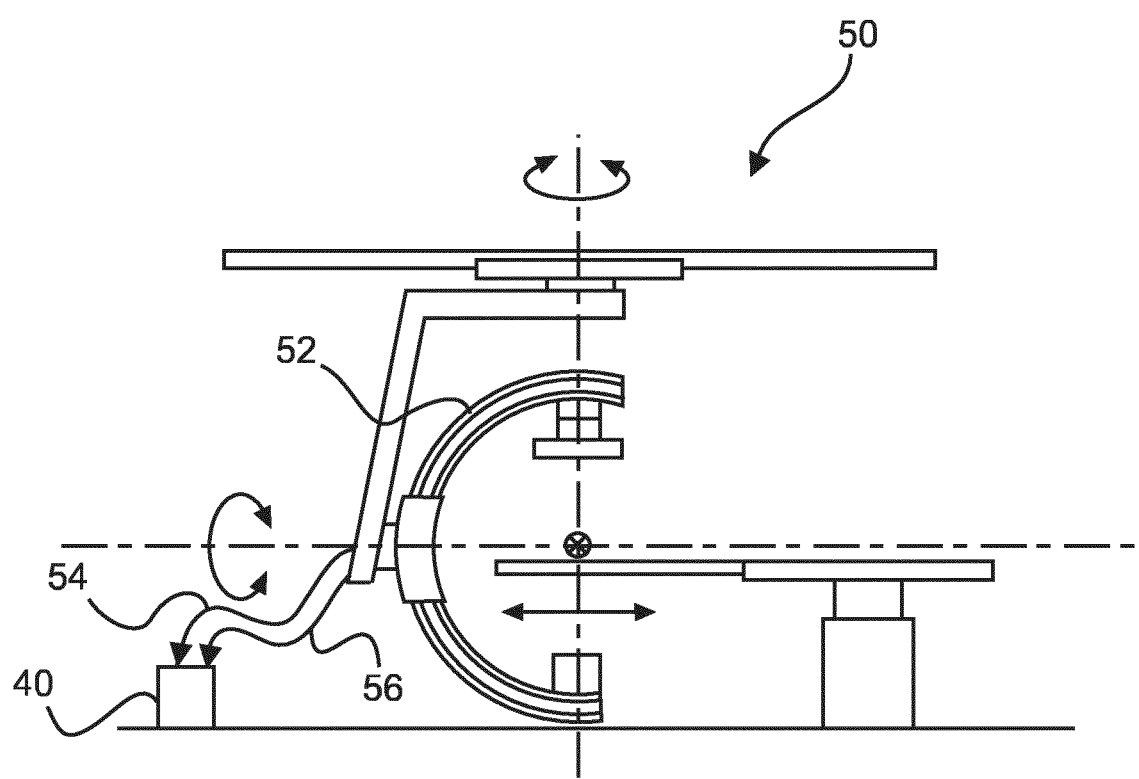
FIG. 6 shows a schematic set up an example of a medical imaging system for vascular treatment localization and quantification of a part of a vascular structure.

FIG. 6 shows a medical imaging system 50 for automatic vascular treatment localization and quantification of a part of the vascular structure. The system comprises an image acquisition unit 52, and an apparatus 40 for automatic vascular treatment localization and quantification of a part of a vascular structure. The apparatus 40 is provided as an application according to the above-mentioned FIG. 5. The image acquisition unit 52 is configured to provide, as shown by arrow 54, the at least one first image comprising the representation of the region of interest of the vascular structure. The image acquisition unit 52 is also configured to provide, as shown by arrow 56, the at least one second image comprising the representation of the region of interest of the vascular structure. The image acquisition unit 52 is shown as a C-arm angulation arrangement; however in other examples, different types of image (X-ray) acquisition arrangements are used.

In an example, the output unit is configured to display the localization of the at least one region of spatial discrepancy on the at least one reference image.

In an example, the image acquisition unit comprises an X-ray imaging device. For example, a CT arrangement is provided. For example, the image acquisition unit comprises a C-arm CT system. In an example, the image acquisition unit comprises an interventional X-ray system.

In an example, the output unit is configured to output data on a stenosis that has been treated.

In an example, the location of the treated stenosis can be presented on the at least one first image and/or on the at least one second image.

In an example, the output data comprises a Quantitative Coronary Angiography (QCA) of a stenosis before stenting. In an example, the output data comprises a Quantitative Coronary Angiography (QCA) of a stenosis after stenting. Here, the QCA is the relative reduction of, for example, an artery diameter at the stenosis position.

In an example, QCA values associated with a stenosis are presented pre and post intervention. In an example, a list of QCA values associated with different stenosis is presented pre and post an intervention.

In an example, the output data is useable to enable a clinician to determine whether the vascular treatment of intervention was successful.

In an example, the system is used for Percutaneous Transluminal Coronary Angioplasty (PTCA) or Percutaneous Coronary Intervention (PCI) in catheter laboratories to treat cardiac stenosis.

Figure 7:
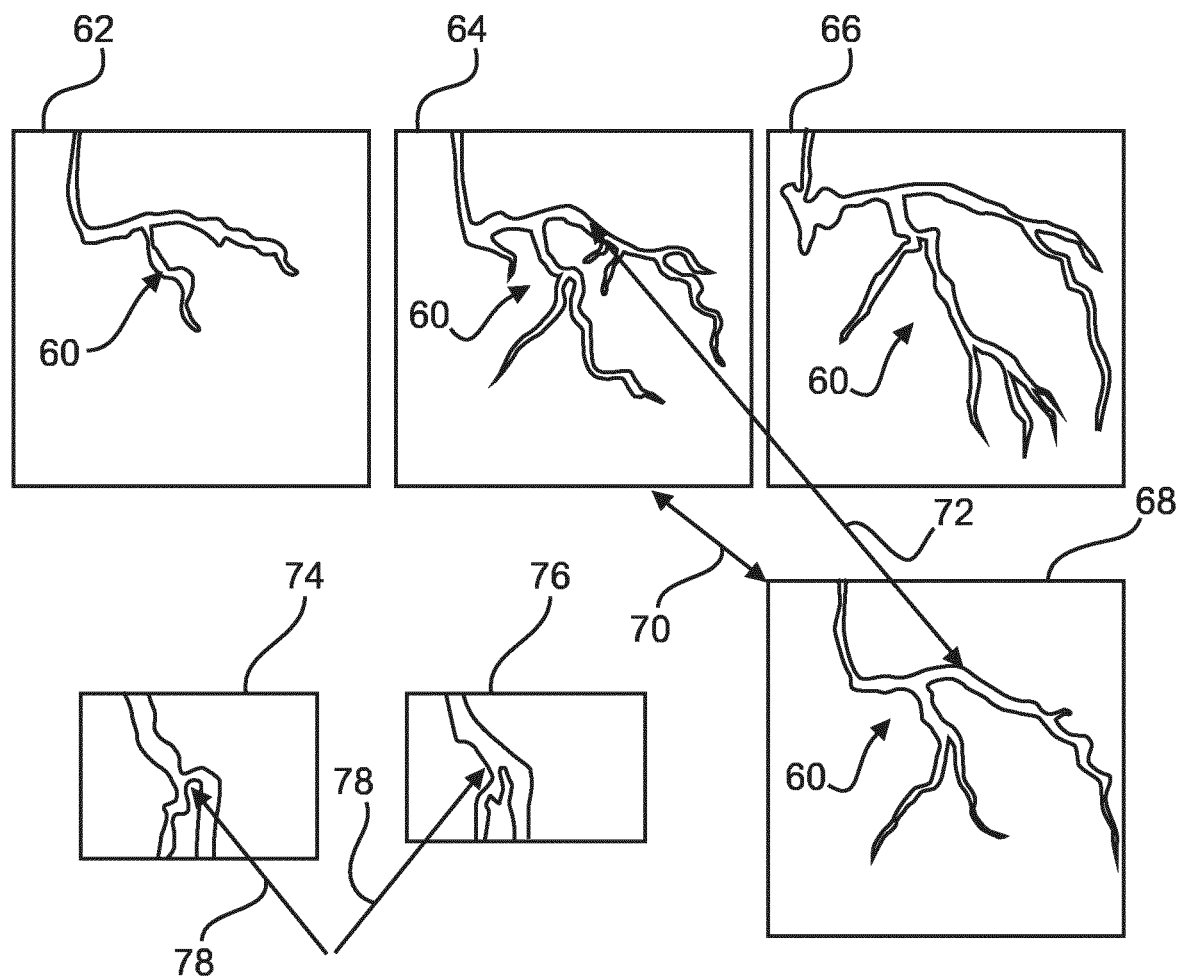
FIG. 7 shows schematic representations of first and second images (before and after a vascular treatment) showing a part of the vascular structure, and useable for vascular treatment localization and quantification of a part of a vascular structure.

FIG. 7 shows representations of first and second images (before and after a vascular treatment) showing a part of the vascular structure. In an upper row, three images 62, 64, 66 are provided as "before" images. Below right, an image 68 is provided as an "after" image. A first arrow 70 indicates a temporal matching being provided; and a second arrow 72 indicates a spatial matching being provided.

A vascular structure 60 is shown in each of the "before" images 62, 64, 66, and the "after" image 68.

Left to the "after" image 68, two portions 74, 76 are shown that relate to the respective region of interest of the vascular structure provided in the before and after images assigned by temporal and/or spatial matching. The two portions 74, 76 are provided for a diameter discrepancy analysis.

A pointer arrow 78 indicates a location of detected discrepancy.

The vascular structure is shown before and after intervention (i.e., pre and post stenting). These images show a region of spatial discrepancy between the images acquired before and after stenting. The region of spatial discrepancy relates to the location of a stenosis. The discrepancy arises because the stenosis is present in the "before" imagery, where the artery is constricted, but in the "after" imagery vascular treatment has led to widening of the artery through for example inflation of a balloon and the deployment of a stent. The before and after imagery are useable, as discussed in relation to FIGS. 1, 2, 3, 4, 5, and 6, for automatic vascular treatment localization and quantification of a part of a vascular structure.

Figure 8:
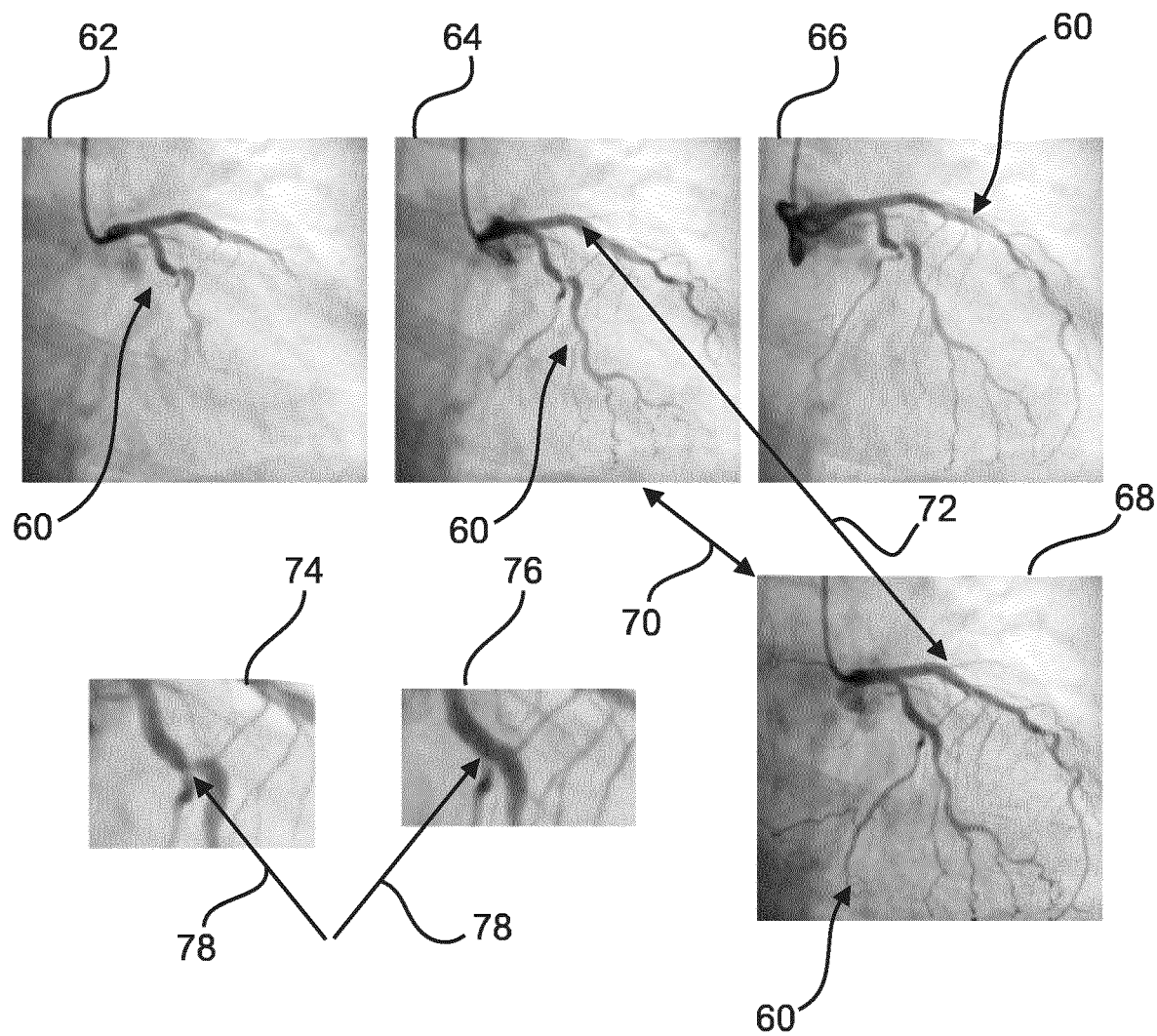
FIG. 8 shows a photographic illustration of the first and second schematic images shown in FIG. 7.

FIG. 8 shows photographic images of the first and second representative images as shown in FIG. 7.

An example, not shown, of a detailed workflow for automatic vascular treatment localization and quantification of a part of a vascular structure is now described. In an angiogram grouping workflow step, all angiograms acquired during a treatment are grouped together following the system geometry. In other words, all the images corresponding to the same system angulation are gathered in the same set. A certain angular tolerance can be fixed, and small angular deviations are accepted. In an angiogram interval selection workflow step, every angiogram of a set is sliced. In this operation, only the consecutive frames that correspond to one or several well injected cardiac cycles are retained. All the others, which correspond to non-injected or insufficiently injected images, are discarded. In a vessel based registration workflow step, within each sliced angiogram set, a registration operation is undertaken. One of the angiograms is taken in turn as a reference. Then for every remaining element of the set, an alignment procedure is undertaken, where every image of the remaining element is paired to an image or frame of the reference. This pairing accounts for breathing, patient motion and for zoom changes between the acquisition of the reference angiogram and the remaining elements in the set. A spatial-temporal pairing transform is involved in this registration process, so that a transformed angiogram is optimally similar to the reference, where the vessels in both images are as similar as possible. The spatial-temporal pairing transform also compensates for different cardiac states. In other words, an angiogram frame of a reference angiogram is paired to an angiogram frame of an angiogram of the remaining angiogram of the set. In a diameter discrepancy analysis workflow step, every registered sliced angiogram image is compared to its counterpart reference image on the basis of its vessel content. Basically, at every location of the registered angiogram image that is salient enough (vessel-wise), a local vessel diameter is estimated. This diameter is compared to the local vessel diameter estimated at the same location in the reference angiogram. This comparison can involve validating criteria, such as local angle agreement. The (validated) diameter difference is recorded at this location. This creates a diameter difference image, which is in turn spatially filtered to identify local areas of high diameter discrepancies. Areas of high diameter discrepancy can be tracked along the temporal axis of the sliced angiograms in order to reinforce the identification robustness. However, an area, or areas, of revascularization are identified that correspond(s) to a vascular treatment, or to a number of vascular treatments. These areas can then be localized on the reference angiogram. In a result gathering workflow step, since several reference frames of the reference angiogram might contain identified treatment areas, these are projected onto a single reference frame. This amounts to registering every frame of the reference angiogram with one frame of the reference angiogram. This involves an elastic transform, and is essentially a vessel driven registration process. The elastic transform can rely on the vessel saliency measurements described above. In an angiogram marking and automatic QCA workflow step, the positions of a, or a number of, vascular treatment(s) are localized on the reference angiogram, and QCA values are provided relating to the vascular structure at that location both before and after the vascular treatment. For example, QCA values are provided pre and post stenting for the position of an identified treated stenosis.

In another exemplary embodiment, a computer program or computer program element is provided that is characterized by being configured to execute the method steps of the method according to one of the preceding embodiments, an appropriate system.

The computer program element might therefore be stored on a computer unit, which might also be part of an embodiment. This computing unit may be configured to perform or induce performing of the steps of the method described above. Moreover, it may be configured to operate the components of the above described apparatus. The computing unit can be configured to operate automatically and/or to execute the orders of a user. A computer program may be loaded into a working memory of a data processor. The data processor may thus be equipped to carry out the method according to one of the preceding embodiments.

This exemplary embodiment of the invention covers both, a computer program that right from the beginning uses the invention and computer program that by means of an update turns an existing program into a program that uses invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. An apparatus for vascular treatment localization and quantification, the apparatus comprising:
   a processing unit; and
   an output unit;
   wherein the processing unit is configured to receive least one first image comprising a representation of a region of interest of a vascular structure; and to receive at least one second image comprising a representation of the region of interest of the vascular structure, the representations relating to spatial extension information of the vascular structure at least in one image plane;
   wherein, between an acquisition of the at least one first image and an acquisition of the at least one second image, a vascular treatment might have been applied to the region of interest of the vascular structure;
   wherein the processing unit is configured to select at least one reference image from an image set formed from the at least one first image and the at least one second image; and to select at least one sample image from the image set, wherein the at least one sample image is different than the at least one reference image; and to register the at least one sample image with the at least one reference image to provide at least one registered image; and to search for a region of a spatial discrepancy by determining a relative change in a diameter or a size of a feature relating to the vascular structure, between the at least one reference image and the at least one registered image, whereby a location of the vascular treatment can be determined; and
   wherein the output unit is configured to, when there exists at least one region of spatial discrepancy, output data representative of an outcome of the vascular treatment applied at the location.

2. The apparatus according to claim 1, wherein the processing unit is further configured to determine the relative change in the diameter or the size of the feature in the at least one reference image with respect to the at least one registered image.

3. The apparatus according to claim 2, wherein the relative change in the diameter or the size is only determined at a spatial position corresponding to a position of the vascular structure.

4. The apparatus according to claim 3, wherein the processing unit is further configured to select at least two sample images from the image set; and to provide at least two registered images; and to verify that the at least one region of spatial discrepancy exists when a discrepancy in the size or the diameter of the feature is present in a first of the at least two registered images and a discrepancy in the size or diameter of the feature is present in at least a second of the at least two registered images.

5. The apparatus according to claim 1, wherein the at least one first image and the at least one second image are vessel angiograms acquired at the same angulation.

6. The apparatus according to claim 1, wherein the processing unit is further configured to provide the at least one registered image by applying a transform to the at least one sample image.

7. The apparatus according to claim 6, wherein the at least one sample image comprises a plurality of sample images, and wherein the transform is a spatial-temporal pairing transform; and
   wherein the processing unit being configured to provide the at least one registered image comprises pairing a sample image of the at least one sample image with the at least one reference image.

8. A medical system for vascular treatment localization and quantification, the system comprising:
   an image acquisition unit; and
   the apparatus for vascular treatment localization and quantification according to claim 7;

wherein the image acquisition unit is configured to provide the at least one first image and the at least one second image comprising the representation of the region of interest of the vascular structure before and after a vascular treatment.

9. The apparatus according to claim 1, wherein the output unit is configured to display localization of the at least one region of spatial discrepancy on the at least one reference image as a stenting location.

10. The apparatus according to claim 9, wherein the output unit is further configured to output QCA information associated with the stenting location before and after the vascular treatment.

11. A method for vascular treatment localization and quantification, the method comprising:
receiving at least one first image comprising a representation of a region of interest of a vascular structure;
receiving at least one second image comprising a representation of the region of interest of the vascular structure;
wherein, between an acquisition of the at least one first image and an acquisition of the at least one second image, a vascular treatment might have been applied to the region of interest of the vascular structure; and wherein the representations of the region of interest of the vascular structure relate to spatial extension information of the vascular structure at least in one image plane;
selecting at least one reference image from an image set formed from the at least one first image and the at least one second image;
selecting at least one sample image from the image set formed from the at least one first image and the at least one second image, wherein the at least one sample image is different to the at least one reference image;
registering at least one image from the at least one sample image with the at least one reference image to provide at least one registered image;
searching for a region of spatial discrepancy by determining a relative change in a diameter of a feature relating to the vascular structure between the at least one reference image and the at least one registered image; and
when there exists at least one region of spatial discrepancy, outputting data representative of an outcome of the vascular treatment applied in the at least one region of spatial discrepancy as the region of interest.

12. The method of claim 11, further comprising:
determining the relative change in the diameter of the feature in the at least one reference image with respect to the at least one registered image.

13. The method of claim 12, wherein the discrepancy in diameter is determined at a spatial position corresponding to a position of the vascular structure.

14. The method of claim 13, further comprising:
verifying that a region of spatial discrepancy exists when a discrepancy in the diameter of the feature is present in a first of the at least two registered images and a discrepancy in the diameter of the feature is present in at least a second of the at least two registered images.

15. A non-transitory computer readable medium having stored thereon software instructions for vascular treatment localization and quantification that causes the processor to execute a method comprising:
receiving at least one first image comprising a representation of a region of interest of a vascular structure;
receiving at least one second image comprising a representation of the region of interest of the vascular structure, wherein a vascular treatment might have been applied to the region of interest of the vascular structure between an acquisition of the at least one first image and an acquisition of the at least one second image, and wherein the representations of the region of interest of the vascular structure relate to spatial extension information of the vascular structure at least in one image plane;
selecting at least one reference image from an image set formed from the at least one first image and the at least one second image;
selecting at least one sample image from the image set formed from the at least one first image and the at least one second image, the at least one sample image being different to the at least one reference image;
registering at least one image from the at least one sample image with the at least one reference image to provide at least one registered image;
searching for a region of spatial discrepancy by determining a relative change in a diameter of a feature relating to the vascular structure between the at least one reference image and the at least one registered image; and
when there exists at least one region of spatial discrepancy, outputting information representative of an outcome of the vascular treatment applied in the at least one region of spatial discrepancy as the region of interest.

\* \* \* \* \*